US011051641B2

(12) United States Patent
Schucker et al.

(10) Patent No.: US 11,051,641 B2
(45) Date of Patent: Jul. 6, 2021

(54) SMART BOTTLE

(71) Applicant: RIPRUP Company S.A., St. Peter Port (GG)

(72) Inventors: Josef Schucker, Ronco Sopra Ascona (CH); Monique Bissen, Pforzheim (DE)

(*) Notice: Subject to any disclaimer, the term of this patent is extended or adjusted under 35 U.S.C. 154(b) by 3 days.

(21) Appl. No.: 16/043,508

(22) Filed: Jul. 24, 2018

(65) Prior Publication Data
US 2019/0021529 A1    Jan. 24, 2019

(30) Foreign Application Priority Data

Jul. 24, 2017   (EP) ..................................... 17182881
Jul. 16, 2018   (EP) ..................................... 18183785

(51) Int. Cl.
*A47G 19/12*       (2006.01)
*B65D 51/24*       (2006.01)
(Continued)

(52) U.S. Cl.
CPC .......... *A47G 19/12* (2013.01); *A47G 19/2227* (2013.01); *A47G 19/2272* (2013.01);
(Continued)

(58) Field of Classification Search
CPC ................ A47G 19/12; A47G 19/2227; A47G 19/2272; A47G 23/16; A47G 2019/2238;
(Continued)

(56) References Cited

U.S. PATENT DOCUMENTS 7,713,482 B2 *   5/2010   Rinker ...................... A23L 2/52
                                                             422/430
9,334,150 B1 *   5/2016   Ost ........................ B67D 1/1236
                          (Continued)

FOREIGN PATENT DOCUMENTS

WO   WO-2016042562 A2 *   3/2016   ......... A47G 19/2227
WO      2016/090235 A1    6/2016
                          (Continued)

OTHER PUBLICATIONS

EPO: "European Search Report"; Application No. EP 18183785; dated Nov. 22, 2019.
(Continued)

*Primary Examiner* — Timothy L Maust
*Assistant Examiner* — Christopher M Afful
(74) *Attorney, Agent, or Firm* — Bryan W. Bockhop; Bockhop Intellectual Property Law, LLC

(57) ABSTRACT

The invention discloses portable beverage vessel for storing beverage to be consumed by a human, having a beverage container in which the beverage is stored; and an electronic device having a vessel controller, a transmitter and a receiver, said vessel controller being adapted to communicate with a beverage dispenser by exchanging messages using the transmitter and receiver of the electronic device; wherein the vessel controller is adapted to send an identification message to the beverage dispenser, by which the beverage dispenser can identify the portable beverage vessel. The invention also discloses a communicating between the portable beverage vessel and a fluid dispenser and a personal electronic device.

18 Claims, 9 Drawing Sheets

(51) Int. Cl.
*B65D 55/02* (2006.01)
*B65D 39/12* (2006.01)
*A47G 23/16* (2006.01)
*A47G 19/22* (2006.01)
*G16H 20/30* (2018.01)
*G16H 20/60* (2018.01)
*H04B 1/02* (2006.01)
*G08B 5/36* (2006.01)
*G08B 7/00* (2006.01)
*G01F 23/00* (2006.01)
*G01F 23/26* (2006.01)

(52) U.S. Cl.
CPC ............. *A47G 23/16* (2013.01); *B65D 39/12* (2013.01); *B65D 51/245* (2013.01); *B65D 55/02* (2013.01); *G16H 20/30* (2018.01); *G16H 20/60* (2018.01); *A47G 2019/225* (2013.01); *A47G 2019/2238* (2013.01); *A47G 2019/2244* (2013.01); *A47G 2200/066* (2013.01); *A47G 2200/08* (2013.01); *A47G 2200/085* (2013.01); *A47G 2200/166* (2013.01); *A47G 2200/183* (2013.01); *A47G 2200/205* (2013.01); *A47G 2200/226* (2013.01); *G01F 23/0015* (2013.01); *G01F 23/0076* (2013.01); *G01F 23/263* (2013.01); *G08B 5/36* (2013.01); *G08B 7/00* (2013.01); *H04B 1/02* (2013.01)

(58) Field of Classification Search
CPC ...... A47G 2019/2244; A47G 2019/225; A47G 2200/066; A47G 2200/08; A47G 2200/085; A47G 2200/166; A47G 2200/183; A47G 2200/205; A47G 2200/226; G16H 20/30; G16H 20/60; B65D 39/12; B65D 51/245; B65D 55/02; G01F 23/0015; G01F 23/0076; G01F 23/263; G08B 5/36; G08B 7/00; H04B 1/02

See application file for complete search history.

(56) References Cited

U.S. PATENT DOCUMENTS

| | | | |
|---|---|---|---|
| 2007/0100666 | A1* | 5/2007 | Stivoric ................... A61B 5/01 705/3 |
| 2014/0374438 | A1* | 12/2014 | Carpenter .............. G16H 20/60 700/236 |
| 2016/0025545 | A1* | 1/2016 | Saltzgiver ........... G01F 23/2962 73/304 C |
| 2016/0194125 | A1 | 7/2016 | Bentkovski |
| 2016/0264395 | A1* | 9/2016 | Hortin ...................... B67D 7/84 |
| 2016/0270717 | A1* | 9/2016 | Luna .................... A61B 5/7246 |

FOREIGN PATENT DOCUMENTS

| | | |
|---|---|---|
| WO | WO 2016/090235 A1 | 6/2016 |
| WO | 2016/155538 A1 | 10/2016 |
| WO | WO 2016/155538 A1 | 10/2016 |

OTHER PUBLICATIONS

Israel Patent Application Office Action; Oct. 4, 2018 (not translated, but submitted to show photograph of bottle cited in corresponding Israeli application).

Photograph of bottles, cited in corresponding Israeli application, publication date unknown to Applicant but believed to be prior to priority date of present application.

Taiwanese Patent Application Office Action; Jun. 13, 2018 (not translated, but submitted to show photograph of bottles cited in corresponding Taiwanese application).

Photograph of bottle, cited in corresponding Taiwanese application, publication date unknown to Applicant but believed to be prior to priority date of present application.

* cited by examiner

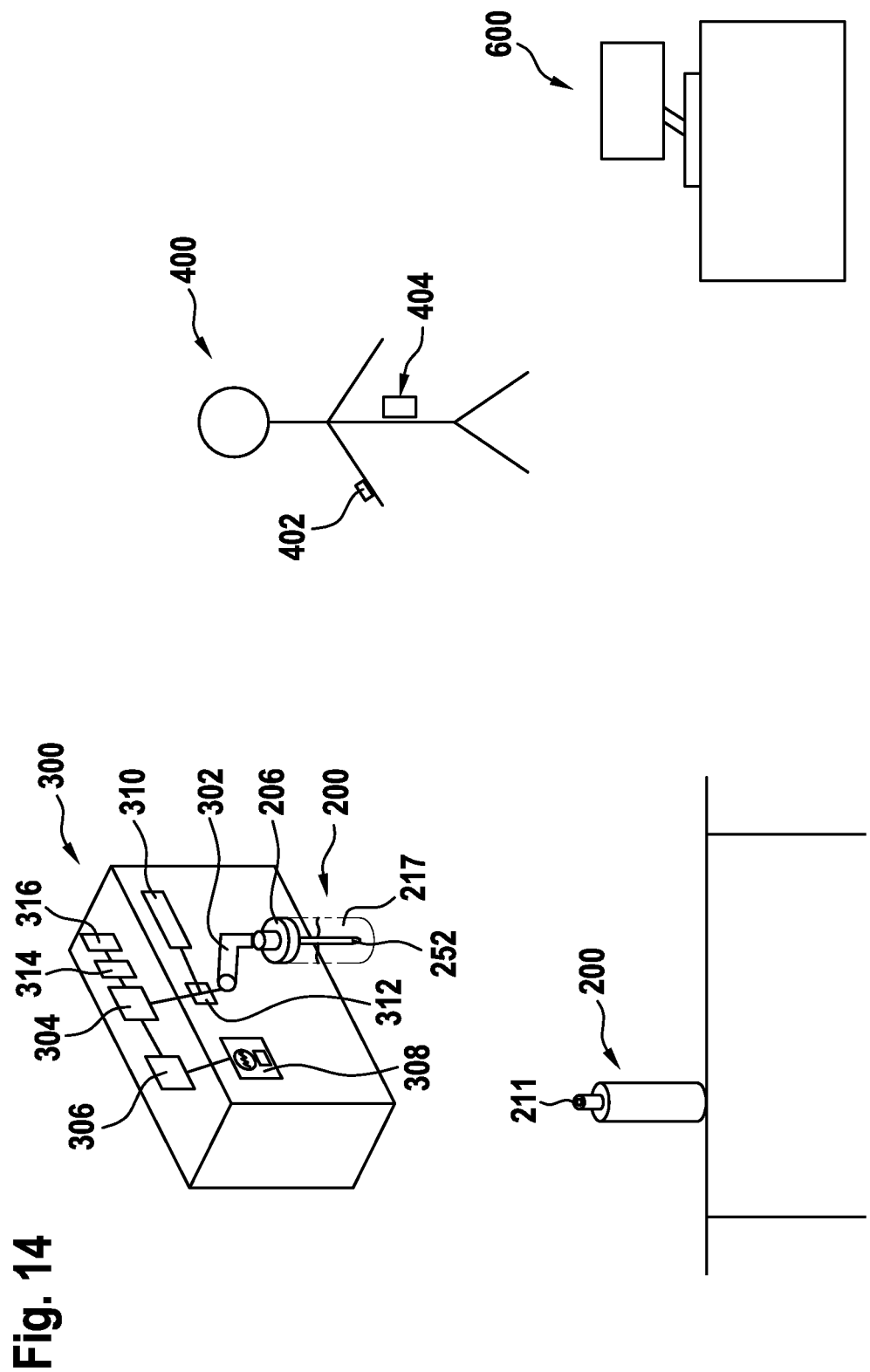

SMART BOTTLE

CROSS-REFERENCE TO RELATED APPLICATION(S)

This application claims the benefit of European Patent Application Nos. EP17182881.7, filed Jul. 24, 2017, and EP18183785.7 filed Jul. 16, 2018 the entirety of each of which is hereby incorporated herein by reference.

BACKGROUND OF THE INVENTION

1. Field of the Invention

The present invention relates to a smart bottle or smart portable beverage vessel for monitoring the water consumption of a user of the bottle and for ensuring that a beverage of reasonable quality is provided to the user.

Depending on the physical activity of the user a user has to drink a certain amount of water comprising certain types and amounts of minerals.

2. Description of the Related Art

Generally, water is consumed by humans increasingly from bottles, since tap water is not considered to be tasty or is more or less polluted. These circumstances cause negative effects. A big share of the bottles is plastic bottles. Such plastic bottles emit substances hazardous to health. Further, the environment is polluted by plastic bottles.

In the heat the summer the plastic bottle may get very hot, even during delivering the bottle to a customer. Thereby, even more substances hazardous to health can be emitted from the plastic to the water. Plastic is a nutrient medium for bacteria multiplying in the heat of the bottle. Accordingly, the quality of water in the bottle is unknown.

WO 2016/090235 A1 relates to a portable vessel, wherein additives located in containers can be added to water in the vessel. The system has the disadvantage, that the quality of the water cannot be monitored and that it is intricate to the user to carry a comparably bulky drinking vessel with a plurality of containers throughout their working days and leisure days.

WO 2016/155538 A1 discloses a vessel that can monitor drinking events.

It is an object of the present invention to provide a smart portable beverage vessel that can increase the comfort of the user and support the health of the user.

SUMMARY OF THE INVENTION

The object of the present invention is solved by a portable beverage vessel according to claim 1, a method according to claim 18 and a beverage dispenser by claim 29.

A smart portable beverage vessel for storing beverage to be consumed (drunken) by a human comprises a beverage container and an electronic device. A beverage vessel in the sense of the present invention may be a bottle or carafe that can be carried by the user and/or used in a household, office or the like. The user may also carry the beverage vessel according to the present invention during its activities such as sports, hiking, traveling, all day activities, touristic activities or the like. The beverage vessel is adapted to cooperate with a beverage dispenser. The beverage dispenser is adapted to cooperate with a plurality of beverage vessels, wherein the beverage dispenser refills the portable beverage vessel positioned by a user for refilling at the beverage dispenser. The beverage dispenser is stationary and each of the plurality of portable beverage vessels is movable with respect to beverage dispenser.

In the beverage container of the beverage vessel a beverage is stored. The electronic device comprises a vessel controller, a transmitter and a receiver. The vessel controller is adapted to communicate with the beverage dispenser for exchanging messages using the transmitter and receiver of the electronic device. The vessel controller is adapted to send an identification message to the beverage dispenser, by which the beverage dispenser can identify the portable beverage vessel. The identification message may comprise any data that may be suitable to identify the portable vessel controller and/or a user of the portable vessel controller. The identification message may comprise a unique identifier, such as a serial number. Alternatively and additionally the identification message may comprise arbitrary data input by a user, such as the name of the user.

Since the portable beverage vessel can be identified by the beverage dispenser, the beverage dispenser can dispense beverage that is best suited to the user and/or the beverage dispenser can recommend the user which beverage may be best suited to the user. Further, the beverage dispenser can identify the user by the beverage vessel and can suggest the user beverages according to his preferences and/or physiological requirements. Further, the beverage dispenser can recommend the user to pour out the remaining beverage in the beverage vessel and/or to clean the beverage vessel, if the beverage has been too long in the beverage vessel and/or if the temperature in the beverage container was too high.

The portable beverage vessel may comprise a fill level sensor adapted to determine the level of beverage in the beverage vessel, wherein the fill level sensor is coupled with the vessel controller. The portable beverage vessel may further comprise a first temperature sensor adapted to determine the temperature of the beverage in the beverage vessel, wherein the first temperature sensor is coupled with the vessel controller. According to one embodiment of the present invention the fill level sensor and the first temperature sensor are not in contact with the beverage in the beverage container. In one embodiment the fill level sensor and the first temperature sensor are integrally formed, i.e. the fill level sensor and first temperature sensor are formed by a single component that is placed on the outside of the beverage container. The fill level sensor may determine the fill level based on the weight of the beverage in the beverage container.

By placing the fill level sensor and the first temperature sensor on the outside of the beverage container, high hygienic standards may be achieved, since the beverage in the beverage container does not get into contact with plastics. Thereby, no platicisers, which are harmful to health are released into the water.

Alternatively or additionally, the portable beverage vessel may comprise a second temperature sensor, i.e. a vessel environment temperature sensor, determining the temperature of the air surrounding the portable beverage vessel. Alternatively or additionally, the portable beverage vessel may comprise a humidity sensor determining the humidity of air surrounding the portable beverage vessel, i.e. a vessel environment humidity sensor. Alternatively or additionally, the portable beverage vessel may comprise a brightness sensor determining the brightness in the environment of the beverage vessel. Alternatively or additionally, the portable beverage vessel may comprise an air pressure sensor determining air pressure of the environment of the beverage vessel.

In one embodiment the beverage container may comprise a display element coupled with the vessel container and an inertia sensor coupled with the vessel controller. The vessel controller is adapted to activate the display element if the inertia sensor detects a movement of the portable beverage vessel. The vessel controller may also be adapted to activate the display element up to a predetermined time span has lapsed after the inertia sensor detects a movement of the portable beverage vessel. Alternatively or additionally the vessel controller may be adapted to activate the display element, if the inertia sensor detects that the beverage vessel is held in at least one predetermined position. The inertia sensor may be any sensor capable of detecting a movement of the portable beverage vessel, such as a motion sensor, an acceleration sensor or the like. Battery charge can be saved, if the display element is only activated, if the vessel is moved or has been moved.

The controller of the portable beverage vessel may be adapted in one embodiment to determine the quality of the beverage in the beverage container by monitoring the temperature by the first temperature sensor and/or the time period during which the beverage is in the beverage container. The vessel controller is also adapted to output a beverage quality signal, if the quality of the beverage in the beverage container is below a predetermined threshold. The time span during which the beverage is in the beverage container may be determined by the vessel controller based on receiving a refill event message from the beverage dispenser and/or a personal electronic device associated to the portable beverage vessel and/or the user of the portable beverage vessel. The personal electronic device may be a smart phone, a tablet computer, a smart watch, a wearable computer or the like.

The controller of the portable beverage vessel may be adapted in one embodiment to determine the quality of the beverage in the beverage container by monitoring the temperature by the second temperature sensor and/or the time period during which the beverage is in the beverage container. The vessel controller is also adapted to output a beverage quality signal, if the quality of the beverage in the beverage container is below a predetermined threshold. The time span during which the beverage is in the beverage container may be determined by the vessel controller based on receiving a refill event message from the beverage dispenser and/or a personal electronic device associated to the portable beverage vessel and/or the user of the portable beverage vessel. The controller can estimate the temperature of the beverage in the beverage container based on the temperature of air surrounding the portable beverage vessel.

The vessel controller may be adapted to monitor the temperature of air surrounding the portable beverage vessel by the second temperature sensor. The vessel controller is adapted to generate a temperature profile of air temperature surrounding the portable beverage vessel during a predetermined time span. Thus, the controller may determine the temperature profile to which a user is exposed. Based on the temperature profile, the demand of the user for beverage and/or minerals may be estimated.

The vessel controller is adapted to monitor the movement of the portable beverage vessel by a movement sensor. In one embodiment the movement sensor may be an inertia sensor. The vessel controller is adapted to generate a movement profile of the portable beverage vessel during a predetermined time span. Based on the movement profile, the demand of the user for beverage and/or minerals may be estimated. The controller can determine based on the movement profile whether a user carried the portable beverage vessel or whether the portable beverage vessel is positioned in a refrigerator by combining the temperature profile and the movement profile. By combining the temperature profile and the movement profile, the controller may determine, whether the portable beverage vessel is carried by a user or stored in a refrigerator and/or the user is physically active and/or the uses a means of transport.

The vessel controller may be adapted to monitor the brightness of the environment of the beverage vessel by the brightness sensor. The vessel controller is adapted to generate a brightness profile of the environment of the portable beverage vessel during a predetermined time span. Thus, the controller may determine the brightness profile to which a user is exposed. Based on the brightness profile, the demand of the user for beverage and/or minerals may be estimated.

The vessel controller may be adapted to monitor air pressure of the environment of the beverage vessel by air pressure sensor. The vessel controller is adapted to generate an air pressure profile of the environment of the portable beverage vessel during a predetermined time span. Thus, the controller may determine air pressure profile to which a user is exposed. Based on air pressure profile, the demand of the user for beverage and/or minerals may be estimated.

In another embodiment the vessel controller may issue a warning message, if beverage is filled into the beverage container without receiving a refill event message, since the quality of the beverage filled into the portable beverage vessel and its origin is unknown. Thereby, the user of the beverage vessel may be protected from drinking contaminated beverage that might have been poured by malicious third parties into the portable beverage vessel. The beverage controller may determine by a signal from the fill level sensor that beverage is filled into the beverage vessel. If no refill message has been received from the beverage dispenser before beverage is filled into the beverage vessel, beverage from an unknown source might be filled into the beverage vessel and a warning is issued by the vessel controller.

The beverage quality signal and/or the beverage warning signal may be a message sent to the personal electronic device of the user of the portable beverage vessel, a message sent to the water dispenser, a message sent to a monitoring unit, an audio signal output by a loudspeaker, an optical signal output by the display element and/or a vibration signal generated by a vibration element of the portable beverage vessel.

The portable electronic device may be a cellular phone, a smart phone, a tablet computer or the like. The monitoring unit may be a computer associated to service staff, such as restaurants staff, hotel staff, nursing staff, hospital staff or the like. If the message is received by the monitoring unit, the staff may replace the beverage in the portable beverage vessel with fresh beverage. Since the beverage vessel can be identified by the beverage dispenser, it can be assured, that the appropriate beverage as desired by the user and/or recommended for the user of the beverage is filled into the beverage vessel.

In one embodiment, if the portable beverage vessel is used in a meeting room, conference room, restaurant. The portable beverage vessel may be associated to a plurality of users, such as participants of the meeting, guests at the same table in the restaurant or the like. Alternatively or additionally the beverage vessel may be associated to a room, such as a meeting room, or associated to a table. The portable beverage vessel may be associated to a beverage type, such as the mineralization of a type of water. The portable beverage vessel may provide the plurality of users with fresh beverage. As soon as a message is received at the monitoring unit, indicating that the beverage in the beverage vessel has to be replaced service staff can replace the beverage in the beverage vessel.

The service staff, such as restaurants staff, hotel staff, nursing staff, and hospital staff may also replace the beverage in the portable beverage vessel, as soon as the optical signal is output by the display element for the cases described above with respect to the message sent to the monitoring unit.

The vessel controller may be adapted to transmit by the transmitter of the portable beverage vessel a message indicating amount of beverage that has been consumed from the beverage vessel by the user to an electronic device external to the drinking vessel. The electronic device external to the drinking vessel may be the personal electronic device associated to the user of the portable beverage vessel, the monitoring unit or any other electronic device, such as a computer. The vessel controller is adapted to receive by the receiver of the portable beverage vessel a message from the external electronic device indicating that the user has to drink beverage. The vessel controller is adapted to cause an output of a signal, if the user has to drink beverage. The signal may be an optical signal indicating that the user has to drink beverage on the display element of the portable beverage vessel. The signal may be an audio signal output by the loudspeaker of the portable beverage vessel. The signal may be a vibration signal output by the vibration element of the portable beverage vessel.

In one embodiment the controller may be adapted to transmit the temperature profile and/or the movement profile and/or the humidity profile and/or the brightness profile and/or air pressure profile to the beverage dispenser and/or monitoring unit and/or the external electronic unit. The physical activity of the user may be determined based on the movement profile. Based on the transmitted temperature profile and/or movement profile and/or humidity profile and/or brightness profile and/or air pressure profile, the beverage dispenser and/or the monitoring unit and/or the external electronic unit can determine amount of beverage and/or amount and type of minerals the user has to drink.

Thereby, it can be ensured that the user of the beverage vessel does not get dehydrated, since the user is informed that he has to drink beverage, before he gets dehydrated.

In one embodiment, the vessel controller is adapted to monitor the fill level of the beverage in the beverage container. The vessel controller is further adapted to cause output of the signal, if the fill level of the beverage is below a predetermined level. The signal may be an optical signal indicating that the fill level of the beverage is below a predetermined fill level on the display element of the vessel controller. The signal may be an audio signal output by the loudspeaker of the portable beverage vessel. The signal may be a vibration signal output by the vibration element of the portable beverage vessel. The signal may be a message sent to the personal electronic device associated to the user of the portable beverage vessel. The signal may be a message sent to the water dispenser. The message may be a message sent to the monitoring unit. In the latter case the service staff may refill the vessel container as has been described above with respect to the beverage that has to be replaced since the quality of the beverage has deteriorated.

In one embodiment the beverage container is a bottle shaped container, wherein around a neck of the bottle shaped container a doughnut shaped housing is arranged and wherein at least the vessel controller and an accumulator are arranged in the doughnut shaped housing.

The beverage container does not comprise any plastics and metal and is made of glass, ceramics or porcelain. Thereby, it can be insured that the beverage container cannot contaminate the beverage in the beverage container.

The doughnut shaped container may be removed from the neck of the bottle shaped container for recharging. The accumulator may also serve as a charger for charging an electronic mobile device, such as a smartphone, tablet computer or the like. Preferably, the doughnut shaped housing is made of metal. The doughnut shaped housing may be removed before cleaning the portable beverage vessel, such as in a dish washer. The accumulator may be recharged inductively.

The term bottle shaped container includes any object for storing beverage comprising a first section with a first cross section a second section at the top of the first section, wherein the second section comprises a second cross section smaller than the first cross section. On the top of the second section an opening for pouring the fluid of the bottle shaped container is formed.

The portable beverage vessel may comprise a lid arranged above the doughnut shaped housing. The lid comprises at least one first light transmitting section extending from the upper portion of the lid to the doughnut shaped housing. The light may be transmitted in the neck of the bottle. The display element is arranged in the doughnut shaped housing and emits light into the first light transmission section. Thereby, no contacts have to be provided for transmitting power and electrical signals into the lid.

Alternatively or additionally the display element may be arranged in the doughnut shaped housing and emit light into a second light transmission section arranged around the lid. In one embodiment the display element may comprise a plurality of display subelements. In one embodiment the first display subelement may transmit light into the first light transmission section and a second displayed sub element may transmit light in the second light transmission section. The display element may be a single light emitter such as a LED or laser diode. The display element may comprise a plurality of light emitter, such as a plurality of LEDs or laser diodes. The light emitter may emit light having different colors. The display element may be a screen, such an OLED display.

The light transmission section may comprise hollow sections, glass sections, light guide PMMA, lenses, Fresnel lenses or any element suitable for directing light.

The first light transmission section may extend cylindrical in the lid from the upper portion of the lid to the lower portion of the lid. The second light transmission section may extend cylindrically around the lid. The first light transmission section and the second light transmission section may be arranged point symmetrical around the center of the portable beverage vessels, in other words the roll axis (longitudinal axis) of the first light transmission section, the second light transmission section and the beverage container coincide.

The first light transmission section may comprise an inner thread engaging with the outer threat of the beverage container. The lid can be fastened by the inner thread of the first light transmission section on the outer threat of the neck of the beverage container.

The invention also discloses a smart portable beverage vessel for storing beverage to be consumed by a human comprising a first portion having a first cross section and second portion having a second cross section and an open top section that can be closed by a lid. The top section of the second portion is the opening for filling the portable beverage vessel and for drinking from the portable beverage vessel. The first cross section is larger than the second cross section. The first portion is closed at its bottom. The first portion is open at its top, and the bottom of the second portion is arranged adjacent to the top of the first portion. The portable beverage vessel comprises at least one electronic device and a charge storing device, such as a battery, accumulator or the like, supplying at least one electronic device with charge. With prior art smart portable beverage vessels, the electronic components are generally located at the bottom of the smart portable beverage vessel. If the electronics of the smart portable beverage vessel are located in the top section sensors for measuring properties of the beverage in the portable beverage vessel can be easier integrated. Further, a display device can be connected with less effort with at least one electronic device.

In one embodiment the charge storage device, such as the battery, accumulator or the like, is arranged radially outward of the second portion.

In one embodiment an energy receiving device adapted to receive energy, which is transmitted to the charge storage device may be comprised by the portable beverage vessel. The energy receiving device may be arranged radially outward of the second section.

In one embodiment at least one electronic device, the charge storage device and the energy receiving device can be implemented in one housing, such as a doughnut shaped housing, which is located radially outward of the second portion.

In one embodiment the outer perimeter of the sub-housing accommodating at least one electronic device, the charge storage device and/or the energy receiving device can have the same outer perimeter as the first portion. Such housing can be cleaned efficiently and deposition of dust and dirt can be prevented.

In one embodiment the portable beverage vessel may comprise a holder arranged radially outward of the second portion. The holder can hold a charging device around the portion.

The holder is adapted to hold the portable beverage vessel in an opening of a charging device such that the first portion of the portable beverage vessel is arranged above second portion. In normal use the second portion is arranged above the first portion. During recharging the portable beverage vessel is positioned upside down and the second portion is located below the first portion. Thereby, dust and dirt can be prevented from entering the portable beverage vessel during recharging.

The first portion can be shaped generally cylindrically and the inner edges of the lower face of the second portion and the cylinder barrel of the first portion may be rounded. In one embodiment, the entire lower face of the first portion may be rounded. As a non limiting example, the radius of the surface at the interface between the inner edges of the lower face of the second portion and the cylinder barrel can be larger than 10 mm for a bottle having a diameter of 70 mm. Thereby, the portable beverage vessel can be cleaned more efficiently.

In one embodiment, a metal housing may be placed around the first portion and/or second portion. Thereby, the glass or porcelain of the first and/or second portion may be protected.

In one embodiment the first portion and/or second portion may be manufactured of glass or porcelain. The top of the second portion may comprise a thread made of glass or porcelain. The lid may also be manufactured of glass or porcelain and may comprise a thread engaging with the thread of the second portion.

If the thread of the second portion and the lid is made of glass or porcelain an effective cleaning of the thread is ensured. The lid may comprise an inner thread and the top section of the second portion may comprise an outer thread.

The at least one electronic component may comprise a first determination element adapted to determine amount of beverage drunken by a user. The first determination element may be a fill level sensor, detecting the fill level of the beverage in the portable beverage vessel.

The second determination element may be adapted to determine the minerals that were introduced into the portable beverage vessel. The second determination element may be implemented by a receiver, controller and memory that stores data about the type and amount of minerals introduced into the portable beverage vessel by a message that was sent from a beverage dispenser that dispenses a beverage into the portable beverage vessel, wherein the message is sent to the beverage vessel and/or a personal electronic device associated to the user of the beverage vessel.

The at least one electronic component may comprise a third determination element adapted to determine the level of beverage in the portable beverage vessel. Also the third determination element may be implemented by the fill level sensor mentioned before.

The at least one electronic component may further comprise a fourth determination element adapted to determine the temperature in the portable beverage vessel. The fourth determination element may be a first temperature sensor.

The at least one electronic component may further comprise a transmitter adapted to transmit data from the portable beverage vessel to a personal electronic device and/or a beverage dispenser. The transmitter may transmit data by a wireless protocol, such as Bluetooth, WIFI and the like. The at least one electronic component may comprise a receiver adapted to receive data from the personal electronic device and/or a beverage dispenser. The receiver may use wireless protocols as mentioned before.

The at least one electronic component may comprise a display element to display information for the user.

The at least one electronic component may comprise a controller adapted to communicate with at least one of the first determination element, the second determination element, the third determination element, the fourth determination element, the display element, the transmitter and the receiver.

In one embodiment the controller may be adapted to determine the quality of the beverage in the portable beverage vessel by monitoring the temperature and/or the time period, during which the beverage is in the portable beverage vessel. The higher the temperature, the faster the quality of the water in the portable beverage vessels is deteriorated. The portable beverage vessel may send a message to the personal electronic device and/or may display a warning on the display device, if the water in the portable beverage vessel must not be consumed by the user.

The controller may be adapted to transmit amount of beverage drunken from the portable beverage vessel by the user to the personal electronic device using the transmitter of the portable beverage vessel. The controller is also adapted to receive by the receiver of the portable beverage vessel from the personal electronic device information indicating that the user has to drink beverage. The controller can display on the display element of the portable beverage vessel the information that the user has to drink beverage.

The features of the disclosed beverage vessels may be combined as suitable.

The invention also discloses a method of controlling and monitoring, respectively at least one of a beverage consumption and/or consumption of minerals in the beverage of a user of a portable beverage vessel. The method may comprise the step of transmitting at least one message to a beverage dispenser from a portable beverage vessel to be filled by the beverage dispenser and positioned by the user for refilling the same at the beverage dispenser. The portable beverage vessel may be identified by at least one message. The message may be transmitted by near field communication (NFC), RFID, Bluetooth or the like. The method may be further configured such as has been described before with respect to the beverage vessel.

The method may comprise the step of exchanging messages between the beverage dispenser, the portable beverage vessel and a personal electronic device. The personal electronic device and the beverage vessel are associated to the same user. The method may determine an amount and/or type of beverage to be recommended to the user based on the exchanged messages. Since the portable beverage vessel can determine amount of beverage drunken by the user and the personal electronic device can determine the physical activity of the user, the method can determine, how much beverage and what type of beverage, the user has to drink. Particularly, the user may be informed how much water he has to drink, and which type of minerals shall be in the water.

The method may determine the physical activity of a user. The method determines the amount of beverage that has to be supplied to the user of the portable beverage vessel based on the physical activity of the user. Further, the method determines the type of minerals that have to be supplied to the user by the portable beverage vessel based on the physical activity of the user. The method determines amount of minerals that have to be supplied to the user by the portable beverage vessel based on the physical activity of the user. The method determines amount of beverage, the type of minerals and amount of minerals that have been drunken by the user of the portable beverage vessel. Further, the method determines amount of beverage to be drunken by the user of the portable beverage vessel based on amount of beverage to be supplied to the user and amount of beverage drunken by the user. The method may determine the type of minerals to be drunken by the user of the portable beverage vessel based on the type of minerals to be supplied to the user and the type of minerals drunken by the user. Further, the method determines amount of minerals to be drunken by the user of the portable beverage vessel based on amount of minerals to be supplied to the user and amount of minerals drunken by the user. The method indicates to the user of the portable beverage vessel and the user of the personal electronic device the amount of beverage to be drunken.

Further, the method may indicate to the user of the portable beverage vessel and/or the user of the personal electronic device the type of minerals to be drunk. The method further indicates to the user of the portable beverage vessel and/or the user of personal electronic device amount of minerals to be drunk.

Thereby, the method ensures that the user drinks the type of minerals and amount of minerals that correspond to the physical activity of the user. It is to be understood that the method may also determine amount and type of minerals that are consumed by the user by food and to adapt the type and/or amount of minerals to be drunken by the user.

In one embodiment the steps of determining the physical activity of a user, the step of determining amount of beverage to be supplied to the user of the portable beverage vessel, the step of determining the type of minerals to be supplied to the user of the portable beverage vessel and the step of determining amount of minerals to be supplied to the user of the portable beverage vessel may be executed by a personal electronic device. The personal electronic device may be a smartphone, a smart watch, a tablet computer, a wearable computer or the like. In one embodiment the step of determining amount of beverage, the type of minerals and amount of minerals drunken by the user of the portable beverage vessel is executed by the portable beverage vessel. The smart portable beverage vessel can cooperate with software running on the personal electronic device, such as an app.

The step of indicating to the user of the portable beverage vessel and/or the user of the personal electronic device the type of minerals to be drunken, and the step of indicating amount of minerals to be drunken to the user of the portable beverage vessel and the user of the personal electronic device amount of minerals to be drunken can be executed by a beverage dispenser adapted to fill the portable beverage vessel. In this embodiment the user can select on an input device of the beverage dispenser whether he agrees to drink the suggested type and amount of minerals. The beverage having the suggested type and amount of minerals can be automatically filled into the portable beverage vessel after the user has confirmed the suggestion displayed by the beverage dispenser. In one embodiment also amount of beverage to be drunken by the user may be indicated to the user by the display of beverage dispenser.

In another embodiment the step of indicating to the user of the portable beverage vessel and/or the user of the personal electronic device the type of minerals to be drunken, and the step of indicating to the user of the portable beverage vessel and/or the user of the personal electronic device amount of minerals to be drunken can be executed alternatively or additionally on the personal electronic device. The proposed selection of beverage having the proposed type and amount of minerals is displayed on the personal electronic device. In one embodiment also amount of beverage to be drunken by the user may be indicated to the user by the display of the personal electronic device.

In another embodiment the step of indicating to the user of the portable beverage vessel and/or the user of the personal electronic device the type of minerals to be drunken, and the step of indicating to the user of the portable beverage vessel and/or the user of the personal electronic device amount of minerals to be drunken can be executed by the portable beverage vessel. The proposed beverage having the proposed type of minerals and the proposed amount of minerals can be displayed on the display of the portable beverage vessel. In one embodiment also amount of beverage to be drunken by the user may be indicated to the user by the display of the portable beverage bottle.

The method further comprises the steps of identifying the user, who intends to refill the portable beverage vessel with the beverage dispenser. The step of identifying the user may comprise the step of communicating between the beverage dispenser and the personal electronic device. Alternatively or additionally the step of identifying the user may comprise the step of communicating with the beverage dispenser and the portable beverage vessel.

The method may further comprise the step of proposing the user the type of minerals and amount of minerals. The step of proposing the user the type of minerals and amount of minerals may comprise the step of displaying on the beverage dispenser the proposed minerals and amount of minerals and/or displaying on the personal electronic device the proposed minerals and amount of minerals and/or displaying on the display of the portable beverage vessel the proposed minerals and amount of minerals.

The step of proposing the user the type of minerals and amount of minerals may include the step of displaying a symbol indicating the type of minerals and amount of minerals in the beverage. The symbols may comprise text or a graphical symbol relating to a type of mineral water that comprises the proposed type of minerals and amount of minerals.

The method may comprise the steps of monitoring the temperature of air around the portable beverage vessel and estimating the temperature of the beverage in the beverage vessel based on the temperature of air around the portable beverage vessel.

The method may comprise the steps of monitoring the temperature of air around the portable beverage vessel, generating a temperature profile of air around the portable beverage vessel during a predetermined time span and determining the demand of a user for beverage and/or minerals based on the temperature profile.

The method may comprise the steps of monitoring the movement of the portable beverage vessel, generating a movement profile of the portable beverage vessel during a predetermined time span and determining the demand of a user for beverage and/or minerals based on the movement profile. By combining the temperature profile and the movement profile, the method can determine whether the portable beverage vessel is carried by a user or stored in a refrigerator. For example, if the temperature is below a predetermined temperature over a predetermined time span and no movement is detected during this predetermined time span, the portable beverage vessel may be stored in a refrigerator. By combining the temperature profile and the movement profile, the method may determine, whether the portable beverage vessel is carried by a user or stored in a refrigerator and/or the user is physically active and/or uses a means of transport.

The method may comprise the steps of monitoring the humidity of air around the portable beverage vessel, generating a humidity profile of the humidity of air around the portable beverage vessel during a predetermined time span and determining the demand of a user for beverage and/or minerals based on the humidity profile. In one embodiment the method may determine the demand of the user for beverage and/or for minerals based on combining the temperature profile determined by the beverage vessel and/or the movement profile determined by the beverage vessel and/or the humidity profile determined by the beverage vessel.

In one embodiment the method may monitor a brightness of the environment of the beverage vessel by the brightness sensor. The method generates a brightness profile of the environment of the portable beverage vessel during a predetermined time span. Thus, the method may determine the brightness profile to which a user is exposed. Based on the brightness profile, the demand of the user for beverage and/or minerals may be estimated.

In one embodiment the method may monitor an air pressure of the environment of the beverage vessel by air pressure sensor. The method generates an air pressure profile of the environment of the portable beverage vessel during a predetermined time span. Thus, the method may determine air pressure profile to which a user is exposed. Based on air pressure profile, the demand of the user for beverage and/or minerals may be estimated.

In one embodiment the method may transmit the temperature profile and/or the movement profile and/or the humidity profile and/or brightness profile and/or air pressure profile to the beverage dispenser and/or monitoring unit and/or external electronic unit. Based on the transmitted temperature profile, and/or movement profile and/or humidity profile and/or brightness profile and/or air pressure profile, the beverage dispenser and/or the monitoring unit and/or the external electronic unit can determine amount of beverage and/or amount and type of minerals the user has to drink.

The invention also discloses a beverage dispenser adapted to dispense a beverage into a portable beverage vessel. The portable beverage vessel may be the portable beverage vessel described before. The beverage dispenser comprises a communication device, a controller and a display device. The communication device is adapted to communicate with the portable beverage vessel and/or a personal electronic device associated to a user of the portable beverage vessel. The controller is adapted to receive a message from the portable beverage vessel and to identify the portable beverage vessel by the message.

The controller is adapted to receive and/or determine data about a type of mineral and an amount of minerals that have to be drunken by the user. The display device is adapted to display a proposed type of minerals and a proposed amount of minerals to the user. If the user confirms the proposed types of minerals and the proposed amount of minerals, the portable beverage vessel is filled with a beverage, such as mineral water that comprises the proposed type of minerals and the proposed amount of minerals. The mineral water may be synthetic mineral water. The water dispenser may transmit the types of minerals, amount of minerals and/or amount of the beverage filled into the portable beverage vessel to the personal electronic device and/or portable beverage vessel and/or monitoring unit.

The beverage dispenser may comprise an environment temperature sensor determining the temperature of air surrounding the beverage dispenser and/or an environment humidity sensor determining the humidity of air surrounding the beverage dispenser. Based on the temperature and/or humidity of air surrounding the beverage dispenser the demand of beverage and/or minerals of a user can be determined. This determination can be carried out by the beverage dispenser and/or the personal electronic device and/or the portable beverage vessel.

The beverage dispenser and its components may be configured to execute the method disclosed above.

The invention also discloses a computer program product that is adapted to execute the steps of the method disclosed above, if loaded into a computer comprising a processor and a memory.

The invention also discloses a set comprising the dispenser and the portable beverage vessel described above.

These and other aspects of the invention will become apparent from the following description of the preferred embodiments taken in conjunction with the following drawings. As would be obvious to one skilled in art, many variations and modifications of the invention may be effected without departing from the spirit and scope of the novel concepts of the disclosure.

BRIEF DESCRIPTION OF THE FIGURES OF THE DRAWINGS

The invention is now described with reference to non-limiting figures showing exemplary and non-limiting embodiments in further detail, wherein:

FIG. 14 shows an embodiment of the method and beverage dispenser according to the present invention.

DETAILED DESCRIPTION OF THE INVENTION

Figure 1:
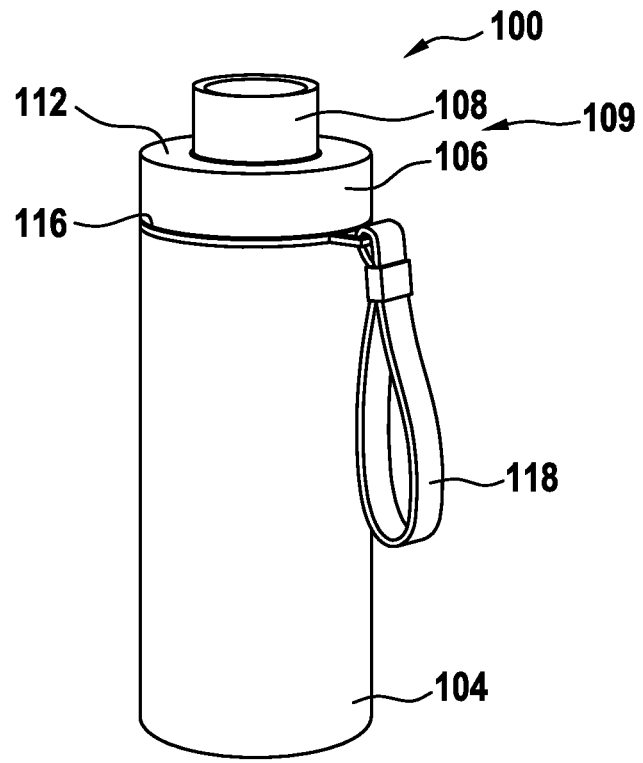
FIG. 1 is a perspective view of the exterior of the beverage vessel according to a first embodiment.

A preferred embodiment of the invention is now described in detail. Referring to the drawings, like numbers indicate like parts throughout the views. Unless otherwise specifically indicated in the disclosure that follows, the drawings are not necessarily drawn to scale. The present disclosure should in no way be limited to the exemplary implementations and techniques illustrated in the drawings and described below. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Under reference to FIGS. 1 to 4 the structure of the portable beverage vessel 100 according to the first embodiment of the present invention is explained.

Figure 2:
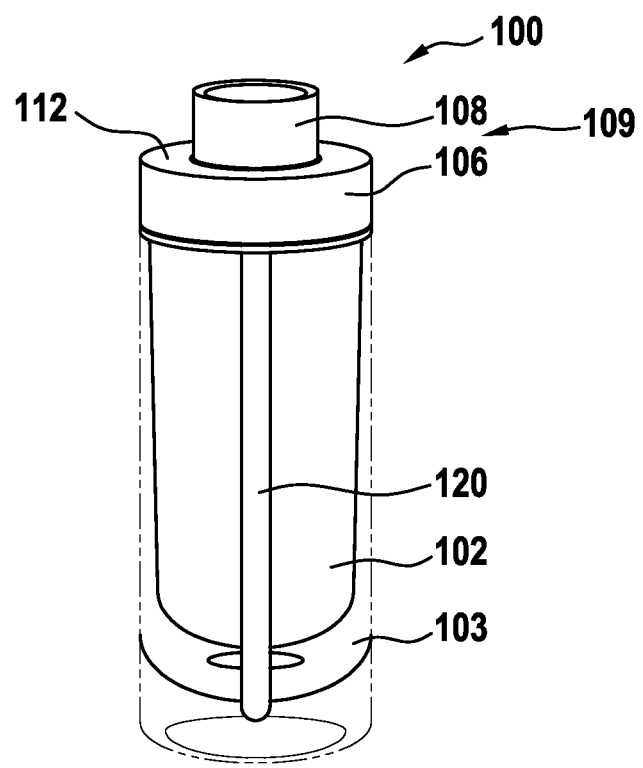
FIG. 2 is a perspective view of the beverage vessel according to the first embodiment showing the interior of the beverage vessel.
Figure 3:
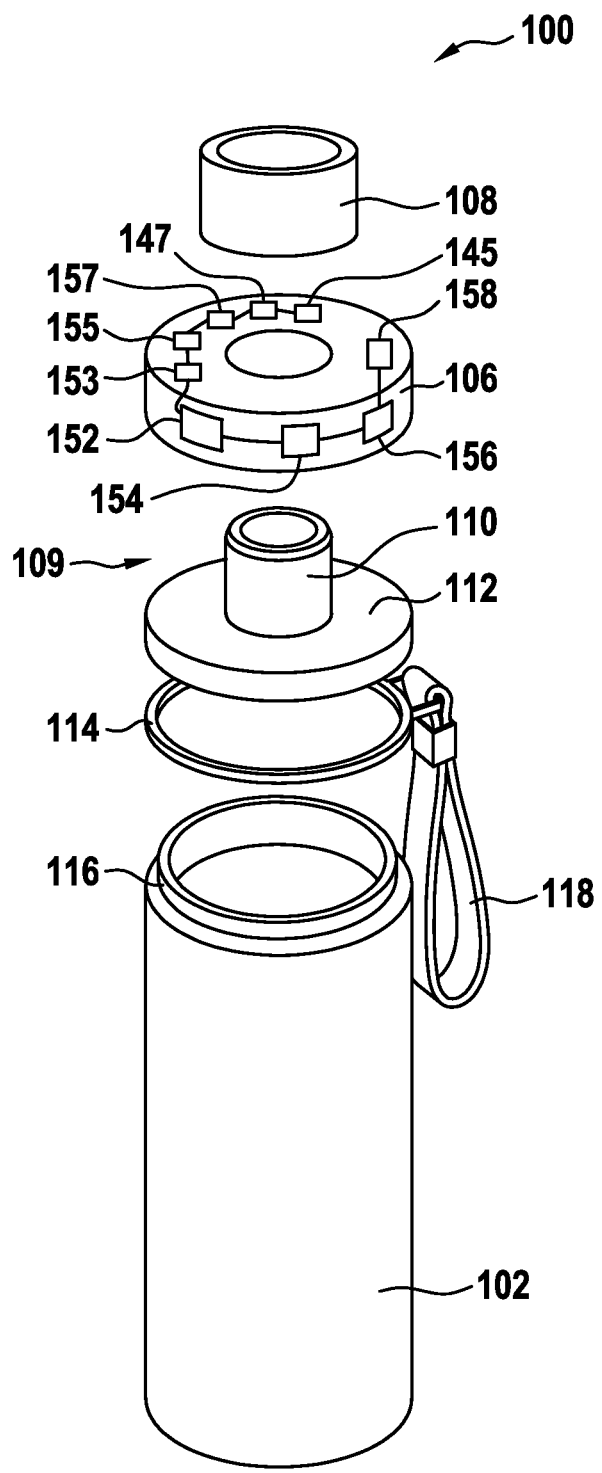
FIG. 3 is an exploded view of the beverage vessel according to the first embodiment.

FIG. 2 shows a first portion 102 of the portable beverage vessel 100 which is a generally cylindrical vessel made of glass, ceramics, or porcelain. The lower section 103 of the cylindrical vessel 102 is rounded, such that it may be easily cleaned by a brush or the like. In the embodiment shown in FIG. 2 the cylindrical vessel 102 is completely rounded at its lower section 103. As shown in FIG. 3., on top of the cylindrical vessel (first portion 102 of the portable beverage vessel 100) a thread 116 is formed, i.e. an outer thread. Adjacent to the top of the cylindrical vessel 102 a sealing 114 is placed. Over the sealing 114 and the cylindrical vessel 102 a closure element 109 is screwed, wherein the closure element 109 comprises an inner thread (not shown) engaging with the outer threat 116 of the cylindrical vessel 102. The closure element 109 may be made of metal such as stainless steel. In one embodiment the closure element 109 may be made of glass or porcelain.

The closure element 109 may comprise a second portion 110 having a smaller diameter than the diameter of the cylindrical vessel 102 (first portion). The upper portion of the second portion 110 may comprise an outer thread that may engage with an inner thread (not shown) of a lid.

The closure element 109 also comprises a cover section 112 covering the opening of the cylindrical vessel 102. The cover section 112 generally extends vertically from the second portion 110 to the perimeter of the closure element 109.

Radially around the second portion 110 a control module 106 is arranged. The control module is generally doughnut shaped and its outer diameter corresponds to the outer diameter of the closure element 109 and/or the sealing 114. The control module 106 comprises a rechargeable battery 152, an inductive coupler 154 for recharging the battery 152, a controller 156 and a transmitter 158.

In use the control module 106 is placed around the second portion 110 of the closure element 109.

As is shown in FIG. 1, a cylindrical housing 104 is placed around the cylindrical vessel 102. The outer diameter of the cylindrical housing 104 corresponds to the outer diameter 106 of the control module 106.

Figure 4:
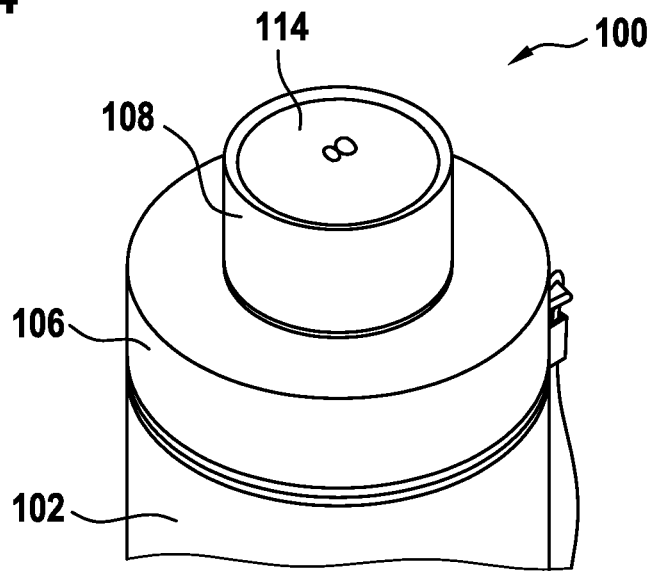
FIG. 4 is a perspective top view of the beverage vessel according to the first embodiment.

As is shown in FIG. 4, the lid 108 may comprise a display 114. On the display information about the status of the beverage in the cylindrical vessel 102 may be displayed, such as the fill level, quality, temperature, mineral concentration, type of minerals or the like. The display 114 may also display information indicating to the user that he has to drink beverage, such as water, which is located in the cylindrical vessel 102.

Turning now again to FIGS. 2 and 3, the controller 156 of the control module 106 is operatively connected with a sensor arrangement 120 extending from the control module 106 to the bottom of the first portion 102 (cylindrical vessel). The sensor arrangement 120 may comprise a fill level sensor, a first temperature sensor or the like.

The control module 106 may also comprise a transceiver 158 comprising a transmitter and a receiver for communicating with an electronic personal electronic device and/or a beverage dispenser being explained below under reference to FIG. 8. The control module 106 and/or controller 156 receive information about amount of beverage filled into the portable beverage vessel, the type of minerals and amount of minerals from the beverage dispensers. This information can be stored in a memory of the portable beverage vessel. In another embodiment the information about amount of beverage filled into the portable beverage vessel, the type of minerals and amount of minerals from the beverage dispensers is transmitted to the personal electronic device.

The control module 106 may further comprise a second temperature sensor 153 determining the temperature of air surrounding the portable beverage vessel 100. The control module 106 may further comprise a humidity sensor 155 determining the humidity of air surrounding the portable beverage vessel 100. The control module 106 may comprise a brightness sensor 147 determining the brightness in the environment of the smart beverage vessel 100. The control module 106 may comprise an air pressure sensor 145 determining air pressure in the environment of the smart beverage vessel 100. The second temperature sensor 153, the humidity sensor 155, the brightness sensor 147 and air pressure sensor may be connected to the controller 156.

Figure 5:
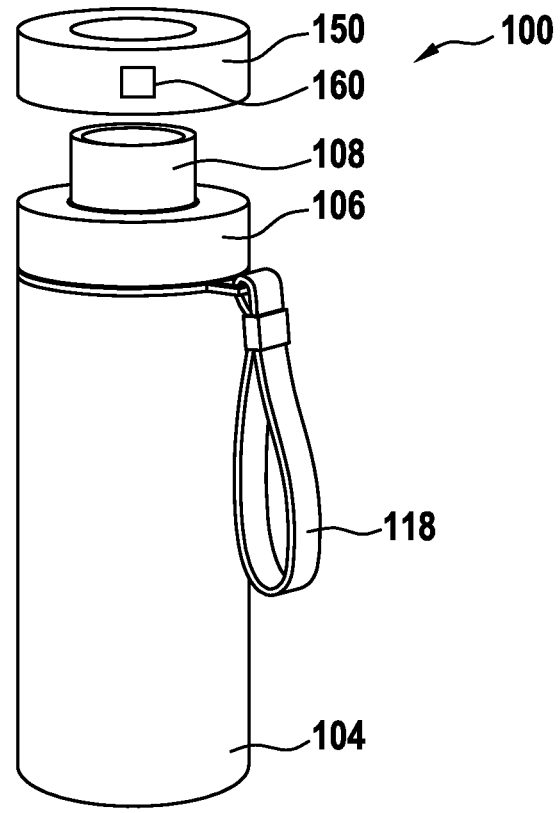
FIG. 5 shows a first embodiment for recharging the beverage vessel.

With reference to FIG. 5 a first embodiment for recharging the rechargeable battery 152 of the portable beverage vessel 100 is shown. A charging module 150, which is generally doughnut shaped is placed around the lid 108 and above the control module 106. The recharging module 150 generates a dynamic magnetic field that induces current in the recharging element (inductive coupler) 154 of the control module 106.

The rechargeable battery 152 of the control module 106 may have a capacity to store charge for operating the portable beverage vessel approximately 6 to 10 days. The recharging module 150 may comprise a second rechargeable battery 160 having a capacity to recharge the rechargeable battery 152 of the control module 106 for up to 4 to 6 times. Further, the recharging module 150 may have a connector to connect a mobile device, such as a smartphone, for recharging the mobile device (personal electronic device).

Figure 6:
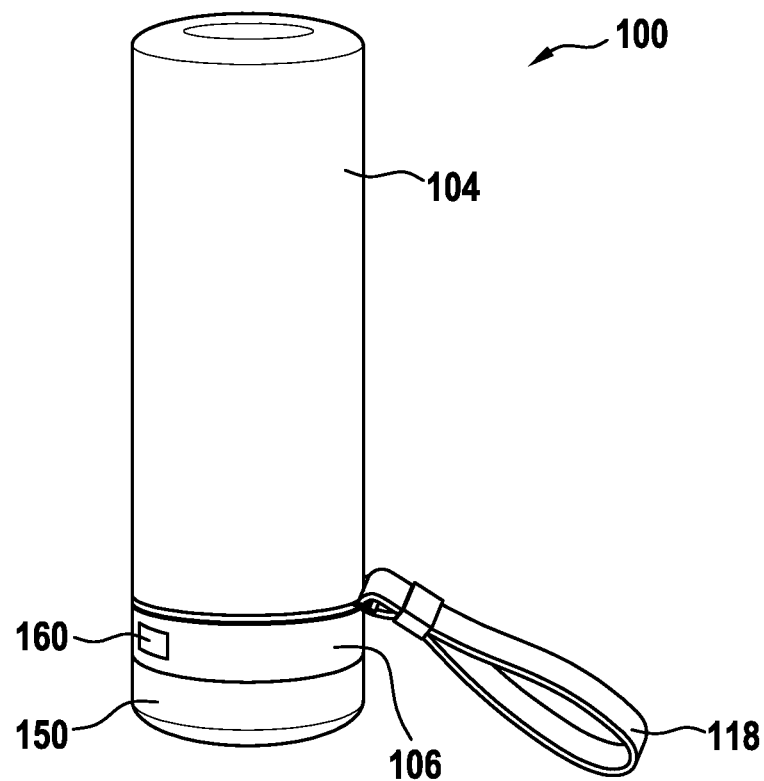
FIG. 6 shows a second embodiment for recharging the beverage vessel.

With reference to FIG. 6, a second embodiment is shown, in which the lid 108 is placed into the recharging module 150 such that the portable beverage vessel 100 according to the present invention is placed upside down into the recharging module 150.

The recharging device 150 may comprise a further connector for connecting the recharging device 152 to a power supply, such as a power grid, to recharge the rechargeable battery 160 of the charging device.

Figure 7:
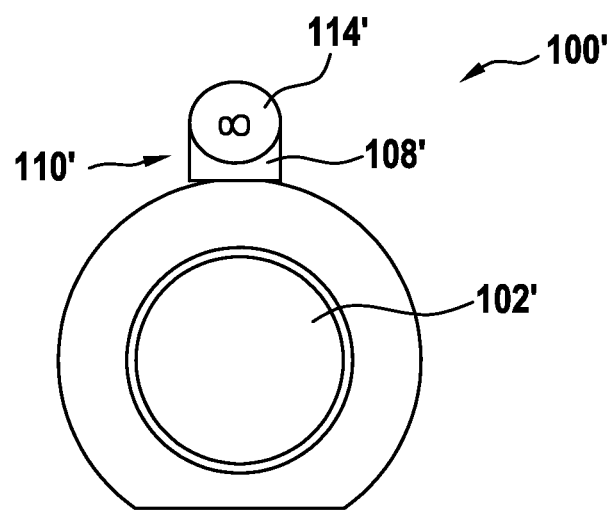
FIG. 7 shows a second embodiment of the present invention.

FIG. 7 shows a second embodiment of the inventive portable beverage vessel. The second embodiment 100' has the style of a beverage vessel that can be transported in a pocket or flask. The first section 102' comprises a larger cross section than the second section 110' on which the lid 108' with the display 114' is placed. The front view of the first portion 102' is generally shaped as a partially cut away disc. It is to be understood, that arbitrary shapes for the first portion 102' can be devised by the person skilled in art.

Figure 8:
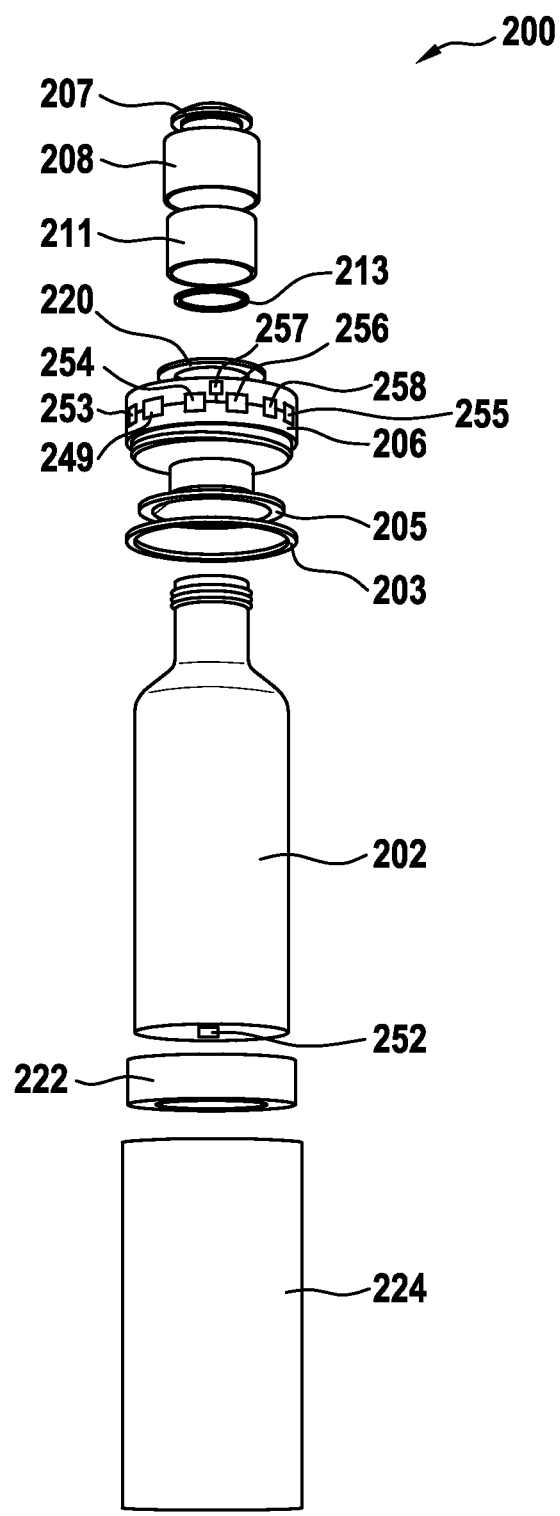
FIG. 8 shows an exploded view of the second embodiment of the beverage vessel.
Figure 9:
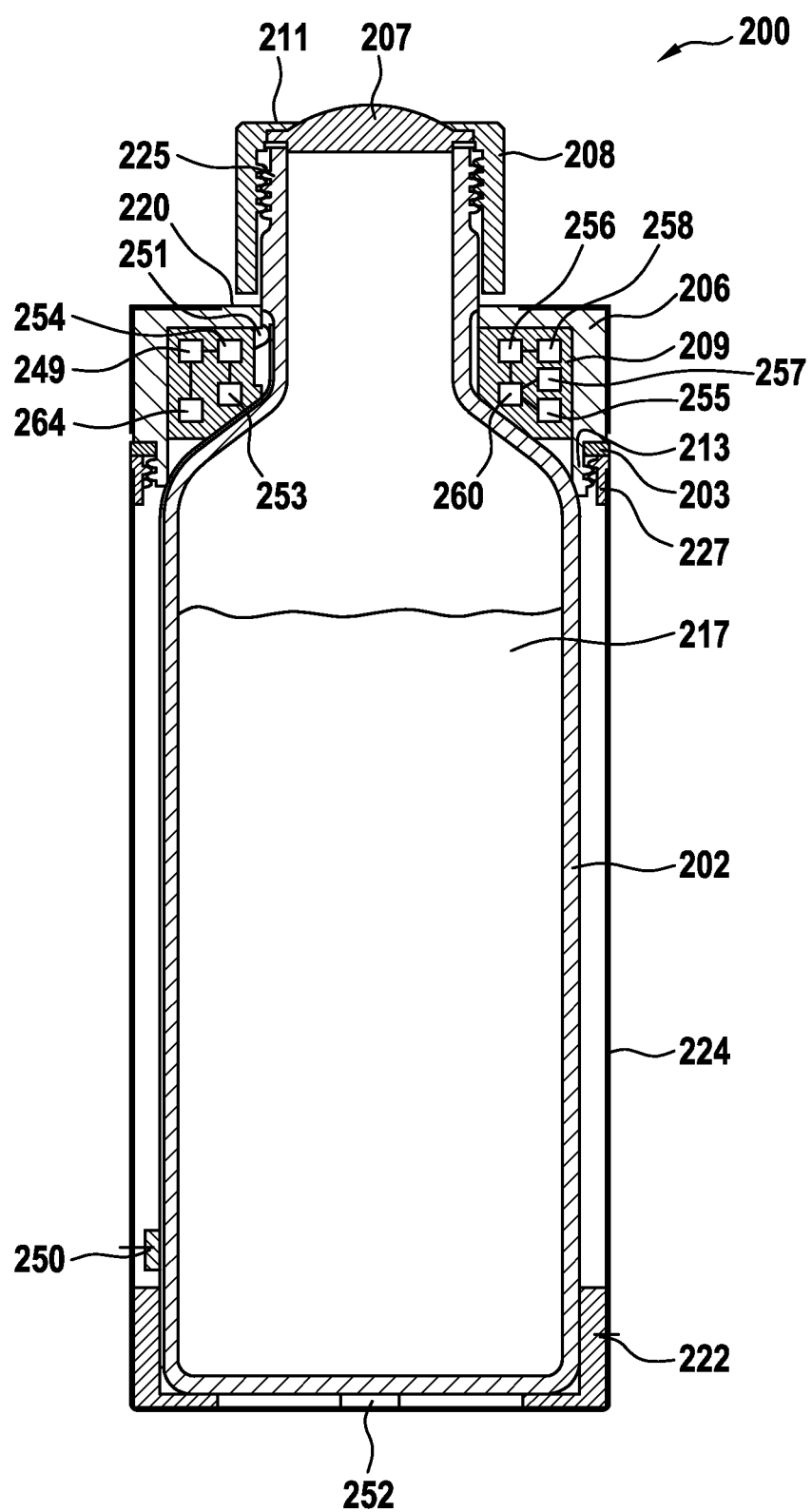
FIG. 9 shows a sectional view of the second embodiment of the beverage vessel.

Reference is made to FIGS. 8 to 11 showing the second embodiment of the drinking vessel 200 according to the present invention. FIG. 8 shows an exploded view and FIG. 9 shows a sectional view of the beverage vessel 200 according to the present invention. As with the first embodiment, the second embodiment may be a smart carafe, smart bottle or the like. The cylindrical sleeve 222 accommodates the bottle shaped beverage container 202 in the cylindrical outer housing 224.

The bottle shaped container 202 functions as a beverage container. The bottle shaped container 202 is made of glass or ceramics and comprises an outer threat at its upper portion, which is formed by the neck 225 of the bottle shaped container. The bottle shaped container is accommodated by a cylindrical sleeve 222, which may be formed by a cylindrical ring having a generally L-shaped cross section, which may be formed of metal, letter, textile, plastics or the like.

At the shoulder of the bottle shaped container a sealing such as an O-ring is disposed. Around the neck 225 of the bottle shaped container 202 the lower part 205 of doughnut shaped housing 206 can be placed. In the doughnut shaped housing 206 a rechargeable battery 249, an inductive coupler 254 for recharging the battery, a controller 256 and a transceiver 258 may be arranged. The rechargeable battery 249, the inductive coupler 254, the controller 256 and the transceiver 258 may be operated as described before with respect to the first embodiment. The doughnut shaped housing may be removed from the bottle shaped container for recharging or cleaning.

In the upper portion of the doughnut shaped housing 206 a transparent ring 220 may be arranged for allowing near field communication to enter the doughnut shaped ring 206, wherein the transparent ring may also serve as a display element. Above the doughnut shaped housing 206 a lid 208 is arranged, wherein the lid 208 comprises a top section 207, a sealing 213 and a first light transmission section 211.

Reference is made to FIG. 9, showing a cross section and the portable beverage vessel 200 according to an embodiment of the present invention. The vessel body 202 is preferably made of glass or any other transparent chemically inert material. Preferably, the vessel body 202 is a cylindrical body. The vessel body is secured by the cylindrical sleeve 222 having an L-shaped cross-section at the outer wall in the outer cylindrical housing 220. The outer cylindrical housing 224 comprises at its upper end an inner threat 227 in which the outer threat 213 of the doughnut shaped housing 206 engages.

The bottle shaped container 202 is held by the doughnut shaped housing 206, the cylindrical sleeve 222 and the outer cylindrical the housing 224 protected against a mechanical impact.

At the outer portion of the bottle shaped container 202 the first temperature sensor 250 and a fill level sensor 252 are arranged measuring the temperature and the fill level of the beverage 217 in the bottle shaped container 202. In one embodiment the fill level sensor 252 may comprise a weight sensor for determining the weight of the beverage in the bottle shaped container 202. The rechargeable battery 249, the inductive coupler 254 for recharging the battery, the controller 265 and the transceiver 258 are arranged in an electronic module 209 housed by the donut shaped housing 206. The controller 256 is electronically connected with the first temperature sensor 250 and the fill level sensor 252. The control module 206 may further comprise a second temperature sensor 253 determining the temperature of air surrounding the portable beverage vessel 200. The control module 206 may further comprise a humidity sensor 255 determining the humidity of air surrounding the portable beverage vessel 200. The control module 206 may comprise a brightness sensor 247 determining the brightness in the environment of the smart beverage vessel 200. The control module 206 may comprise an air pressure sensor 245 determining air pressure in the environment of the smart beverage vessel 200. The second temperature sensor 253, the humidity sensor 255, the brightness sensor 247 and air pressure sensor 245 may be connected to the controller 256. The control module may further comprise an inertia sensor 257 connected to the controller 206.

The controller 256 is also electrically connected to the light emitter 251, such as a LED, a laser diode or the like. The light emitter 251 may comprise a plurality of light emitting elements emitting different colors.

The light emitted by the light emitter is emitted into the bottle neck 225 transmitting the light to the lid 208, where the light is emitted by the first light transmission section 211. The light emitted by the light emitter 251 may also enter into the second light transmission section 220 and exit the second light transmission section 220 arranged around the lid on the donut shaped housing 206.

In the embodiment shown in FIG. 9 a single light transmitter 251 is used to transmit light into the first light transmission section 211 and the second light transmission section 220. It is to be understood that a plurality of light transmitters (not shown) may be used to emit light, wherein at least one of the light emitters emits light that is directed to the first light transmission section 211 and wherein at least one light emitter emits light that is directed to the second light transmission section 220.

The electronic module 209 may further comprise an acceleration sensor 260. The controller 256 can be adapted to activate the light emitter 251 only, if acceleration generation sensor 260 detects that the beverage vessel 202 has been moved or is held in a particular position. Thereby, battery charge can be saved.

The electronic module also comprises a vibration element 264 coupled to the controller 256. The controller can be adapted to activate the vibration element 264, if user has to be informed about an event, such as a decreasing quality of the beverage 217 in the beverage vessel. As soon as the user notices the vibration signal, he may move the beverage vessel and consequently the light emitter 251 is activated for displaying information on the first and second rights transmission sections 211, 220.

Figure 10:
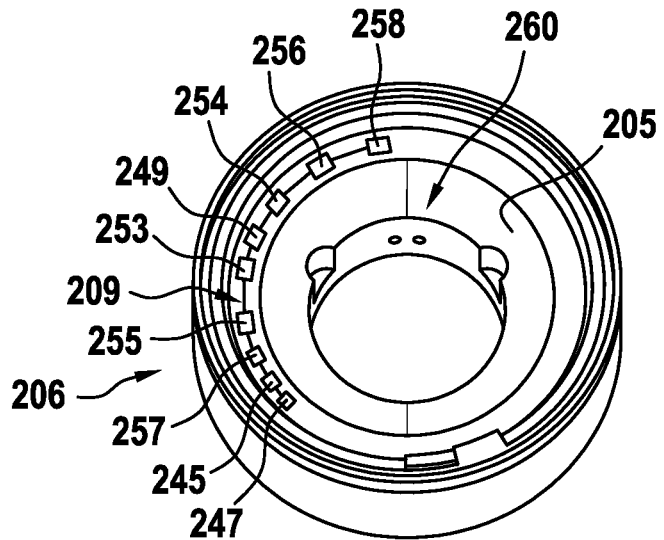
FIG. 10 shows details of the doughnut shaped housing.

Reference is made to FIG. 10 showing the doughnut shaped housing 206 from the side that is directed to the bottle shaped container 202. The lower part of the doughnut shaped housing 205 is formed by the cylindrically tapered housing 205. In the circular opening of the doughnut shaped housing 206 a plurality of contacts 260 are arranged, wherein the contacts 260 of the doughnut shaped housing 206 cooperate with the contacts 251 formed on the sensor arrangement 250, 252 for transmitting electrical signals representing temperature of the beverage in the bottle shaped container and the fill level of the beverage in the bottle shaped container.

Figure 11:
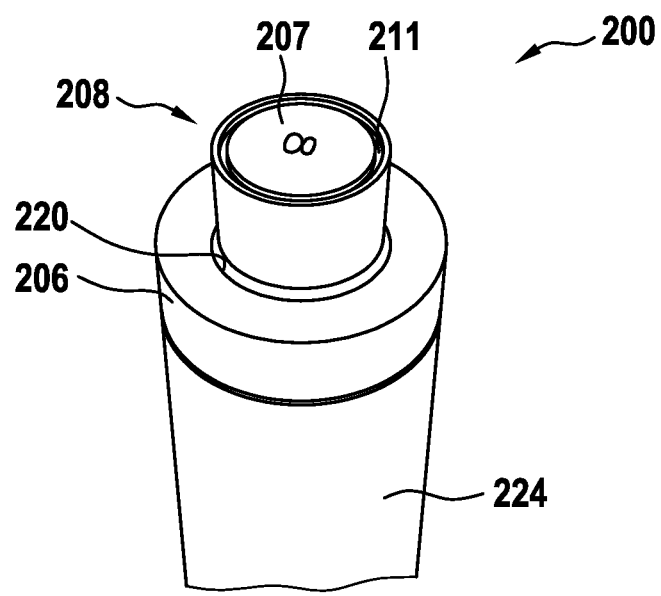
FIG. 11 shows a top view of the beverage vessel.

Reference is made to FIG. 11 showing a top view of the beverage vessel 200. Above the cylindrical outer housing 224 accommodating the bottle shaped container 202 the doughnut shaped housing 206 is arranged around the neck of the bottle shaped container 202. Above the doughnut shaped body 206 the lid 208 is arranged. Around the top portion 207 of the lid 208 a cylindrical first light transmission section 211 is disposed. A display element accommodated by the doughnut shaped housing 206 emits light into the cylindrical first light transmission section 211.

Around the lid 208 the transparent element 220 may be arranged. Through the transparent element 220 electromagnetic waves of near field communication may pass. In one embodiment the transparent element 220 may serves as a second light transmission section.

The display element may be adapted to transmit light into the first and/or a second light transmission section. The display element may transmit continuous light, flashing light or light having a selected of a plurality of selectable colors into the first and/or second like transmission section. In order to code information, as will be described below, the display element may change the color of light transmitted into the first and/or second light transmission section and may transmit continuous light or flashing light depending on the information to be displayed. Depending on the information to be displayed, the frequency of the flashes may change. Further the display element may be formed in one embodiment by a beverage crystal display, a flat screen, or the like that is arranged at the beverage vessel 200.

Figure 12:
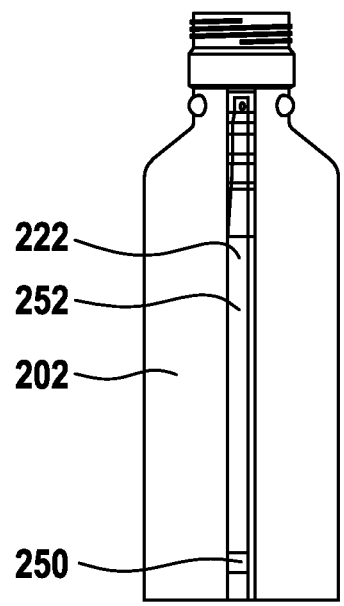
FIGS. 12 and 13 show details of a bottle shaped container functioning as a beverage container according to a third embodiment.
Figure 13:
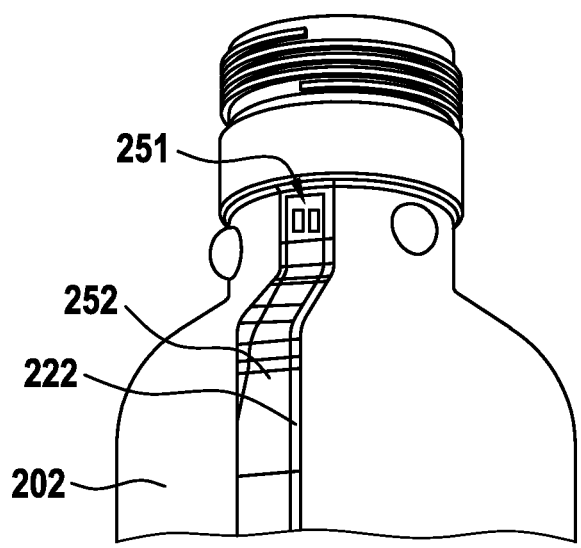

Reference is made to FIG. 12 showing a third embodiment of the bottle shaped container. The bottle shaped container comprises a recess 222 extending from the bottom of the bottle shaped container 202 to the neck of the bottle shaped container. Within the recess the first temperature sensor 250 and/or the fill level sensor 252' such as a capacitive fill level sensor are arranged. As can be seen in FIG. 13, showing details of the neck of the bottle shaped container according to the third embodiment the sensor arrangement formed by the first temperature sensor 250 and the fill level sensor 252' comprises electrical contacts 251 at the upper portion of the fill level sensor 252'.

Reference is now made to FIG. 14 for explaining the method according to the present invention and a stationary water dispenser 300 according to the present invention. The water dispenser 300 of the present invention comprises a communication device 304, a controller 306 and a display device 308. The controller 306 controls the display device 308, the communication device 304, a water generation device 310 and a valve 312. The water generation device 310 may generate synthetic mineral water by individually remineralizing demineralized water by supplementing the demineralized water with dedicated minerals stored in a plurality of mineralization tanks. In another embodiment the water generation device 310 may be connected to a plurality of tanks in which different mineral waters having different mineral mixtures are stored. The valve 312 is adapted to dispense a beverage via the tap 302 into the beverage vessel 200.

The beverage dispenser 300 may comprise an environment temperature sensor 314 determining the temperature of air surrounding the beverage dispenser 300 and/or an environment humidity sensor 316 determining the humidity of air surrounding the beverage dispenser 300. Based on the temperature and/or humidity of air surrounding the beverage dispenser 300 the demand of beverage and/or minerals of a user can be determined. This determination can be carried out by the beverage dispenser 300 and/or a personal electronic device 404 and/or the portable beverage vessel 200.

The personal electronic device 404, such as a smartphone, is associated to a user 400 and carried by the user. The smartphone 404 is coupled with a smart watch 402. The smartphone 404 and/or the smartwatch 402 monitor the physical activity of the user, such as the number of steps. Further, the smart phone 404 and/or the smart watch 402 can monitor the heart frequency. Based on the physical activity of the user a software (app) running on the smartphone 404 and/or on the smartwatch 402 can calculate amount of fluid, type of minerals and/or amount of minerals that have to be supplied to the user 400. The user may also enter food consumed into the software running on the smartphone 404 such that software can calculate amount of beverage, minerals and/or type of minerals that have to be supplied to the user also based on the food consumed.

The fill level sensor 252 can determine how much beverage the user 400 has drunken. The water dispenser 300 can transmit to the controller 256 and/or to the personal electronic device 404 the type of minerals and amount of minerals dispensed by the water dispenser 300 into the smart beverage vessel. The controller 256 can transmit amount of drunken beverage, type of drunken minerals and amount of minerals to the personal electronic device 404 and/or beverage dispenser 300 by the transceiver 258.

The controller 256 monitors the temperature of air around the portable beverage vessel 200 by the second temperature sensor 253 and estimates the temperature of the beverage in the beverage vessel 202 based on the temperature of air around the portable beverage container 206. The controller 256 monitors the temperature of air around the portable beverage vessel 200 by the second temperature sensor 253, generates a temperature profile of air around the portable beverage vessel 200 during a predetermined time span and determines the demand of a user for beverage and/or minerals based on the temperature profile. The controller 256 monitors the movement of the portable beverage vessel by the inertia sensor 257, generates a movement profile the portable beverage vessel 200 and the user of the portable beverage vessel during a predetermined time span and determines the demand of a user for beverage and/or minerals based on the movement profile. By combining the temperature profile and the movement profile, the controller 256 can determine, whether the portable beverage vessel is carried by a user or stored in a refrigerator and/or the user is physically active and/or the user uses a means of transport. For example, if the temperature is below a predetermined temperature over a predetermined time span and no movement is detected during this predetermined time span, the portable beverage vessel may be stored in a refrigerator.

The controller 256 monitors the humidity of air around the portable beverage vessel 200 by the humidity sensor 255, generates a humidity profile of air around the portable beverage vessel during a predetermined time span and determines the demand of a user for beverage and/or minerals based on the humidity profile.

In one embodiment the controller 206 may be adapted to monitor the brightness of the environment of the beverage vessel 200 by the brightness sensor 247. The controller 206 generates a brightness profile of the environment of the portable beverage vessel 200 during a predetermined time span. Thus, the controller 206 may determine the brightness profile to which a user is exposed. Based on the brightness profile, the demand of the user for beverage and/or minerals may be estimated.

In one embodiment the controller 206 may be adapted to monitor air pressure of the environment of the beverage vessel 200 by air pressure sensor 245. The controller 206 generates an air pressure profile of the environment of the portable beverage vessel 200 during a predetermined time span. Thus, the controller 206 may determine air pressure profile to which a user is exposed. Based on air pressure profile, the demand of the user for beverage and/or minerals may be estimated.

In one embodiment the controller 256 can determine the demand of the user for beverage and/or minerals based on combining the temperature profile determined by the beverage vessel 200 and/or the movement profile determined by the beverage vessel 200 and/or the humidity profile determined by the beverage vessel 200 and/or the brightness profile determined by the beverage vessel 200 and/or air pressure profile determined by the beverage vessel 200.

In another embodiment the controller 256 can transmit the temperature profile determined by the beverage vessel 200 and/or the movement profile determined by the beverage vessel 200 and/or the humidity profile determined by the beverage vessel 200 and/or the brightness profile determined by the beverage vessel 200 and/or air pressure profile determined by the beverage vessel 200 to the personal electronic device.

Accordingly, the software running on the personal electronic device (the mobile phone 404) can calculate amount of beverage and/or type of minerals and/or amount of minerals that have to be drunken by the user 400. Such calculation can be based on amount of beverage, type of minerals and/or amount of minerals that have to be supplied to the user 400 as well as amount of beverage, type of minerals and/or amount of minerals that have been consumed by the user 400 from the beverage vessel 200 as well as amount of beverage, type of minerals and/or amount of minerals that have been eaten by the user 400 as entered by the user 400 into the software running on the mobile phone 404. The beverage dispenser 300 transmits the types of minerals and amounts of minerals in the beverage filled into the beverage vessel to the transceiver 258 of the beverage vessel 200, and the controller 256 of the beverage vessel 200 stores values of the types of minerals and amounts of minerals in a memory. Thereby, the controller 256 of the beverage vessel 200 can determine the types and amounts of minerals drunken by the user based on amount of beverage drunken by the user as determined by a fill level sensor 252.

In another embodiment the beverage dispenser 300 transmits the types of minerals and amounts of minerals in the beverage filled into the beverage vessel to the personal electronic device (smart phone and/or smart watch). Thereby, the personal electronic device can determine the types and amounts of minerals drunken by the user based on amount of beverage drunken by the user as determined by a fill level sensor 252 of the beverage vessel 200.

The software running on the mobile phone 404 and/or the controller 306 of the beverage dispenser may calculate amount of beverage, type of minerals and/or amount of minerals that have to be drunken by the user. The controller 306 of the water dispenser 300 may indicate a recommended beverage, such as a recommended type of mineral water on the display 308 of the beverage dispenser. The recommended mineral water may comprise the type of minerals and the amount of minerals that correspond as far as possible to the recommended type of minerals and/or amount of minerals to be drunken by the user. The user can confirm on the touch sensitive display 308 the proposed type of mineral water and thereafter, the controller 306 controls the water generation unit 310 and the valve 312 such that the recommended mineral water is supplied via the tap into the beverage vessel 200.

It is to be understood that the beverage dispenser can cooperate with a plurality of users 400 and beverage vessels 200. The controller 306 may have means for identifying a user 400 by its mobile phone 404 and/or by its beverage vessel 200. For identifying the mobile phone 404 and/or the beverage vessel 200, a wireless communication protocol such as Bluetooth, WiFi or the like may be used.

The beverage vessel 200 may also monitor the quality of the beverage in the vessel body 202 by the first temperature sensor 250. The temperature of the water may be measured by the first temperature sensor. Further, the controller 256 may determine the time span during which the water has been in the beverage vessel 200. If the temperature and/or the time span during which the water is in the beverage vessel exceeds a predetermined time span, a warning for a user is generated, such as by a message displayed on the mobile phone 404 and/or on the smartwatch 402 and/or on the display 211 of the beverage vessel.

The inventive method may also determine whether the user of the beverage vessel 200 has to drink beverage, such as water. The inventive method may display a message on the smartphone 404, the smartwatch 402 and/or the beverage vessel 200, if the inventive method determines that the user has to drink additional beverage. The inventive method may also determine based on the physical activity of the user 400 that the user 400 has to drink additional minerals. If the inventive method determines that the user has to drink additional minerals, a message and/or light signal may be displayed by the mobile phone 404, smartwatch 402 and/or smart beverage vessel 200. The message may also include the recommended type of minerals, amount of minerals and/or the recommended beverage, such as the recommended type of mineral water.

It is an advantage of the present invention that quality of a beverage in a beverage vessel may be monitored. Further, a user can be provided with tailored beverages comprising the type of minerals and amount of minerals that are actually needed by the body of the user by remineralizing demineralized water.

If the controller 256 determines by using the first temperature sensor 250 that the temperature of the beverage 217 exceeds a predetermined threshold, an audio signal can be output by a loudspeaker (not shown). Alternatively or additionally, the controller 256 may activate the light emitter 251 to emit light. Alternatively or additionally the controller 256 may transmit a message by a transceiver 258 to an electronic device 609 associated to service staff, such as hotel staff, restaurants staff, hospital staff, nursing staff or the like. The message may be displayed on the display 604 connected to the electronic device.

As soon as the light emitter 251 emits light or a message is displayed by the electronic device 600, the service staff is notified that the water in the beverage vessel 200 has to be changed.

In one embodiment the controller 256 may monitor the fill level of the beverage 217 the beverage vessel 200. If the fill level of the beverage 217 is lower than a predetermined threshold, the controller may output an audio signal by the loudspeaker. Alternatively or additionally the controller 256 can output an optical signal by the light emitter 251. Alternatively or additionally the controller can transmit a message by the transceiver 258 to the electronic device associated to the service staff mentioned before. By the light emitted by the light emitter 251 and/or the message received by the electronic device 600, the service staff is informed that the beverage in the beverage vessel 200 has to be replaced.

In another embodiment the controller 256 may be adapted to emit light depending on the type of beverage and/or the type and/or amount of minerals in water, such as mineral water, synthetic mineral water or the like. The light emitter 215 may comprise a plurality of light emitting diodes or laser diodes each having a different color. The color of the light emitted by the light emitter may change depending on the signal to be displayed, such as temperature of the beverage 217, fill level of the beverage 217, the type of beverage 217 and/or the time span, during which the beverage was in the beverage vessel 200. The type of beverage 217 and/or the type of minerals and/or amount of minerals that has been filled into the beverage vessel 200 is transmitted by the beverage dispenser 400 via the transceiver 258 to the controller 256 and stored in a memory. In another embodiment, the type of beverage 217 and/or the type of minerals and/or amount of minerals that has been filled into the beverage vessel 200 is transmitted by the beverage dispenser 400 to the personal electronic device (smart phone and/or smart watch).

The controller 256 may be requested by the electronic device 600 associated to a service staff to transmit data about the beverage consumption of the user of the beverage vessel 200. The controller 256 may transmit in response to such request or based on another event, such as lapse of a predetermined time span, amount of beverage, the user had been drinking from the beverage vessel 200 to the electronic device 602 using the transceiver 258. The controller 256 is also adapted to transmit light by the transceiver 215 to be displayed on the first light transmission section 211 and/or second light transmission section 220, if the user has to drink additional amount of beverage.

The first light transmission section 211 and the second light transmission section 220 may be controlled by the controller 256 such information is displayed by the length of an illuminated segment extending in circumferential direction of the first light transmission section 211 and/or the second light transmission section 220. For example, the better the hydration status and/or mineralization status of the user the longer is the illuminated segment. Vice versa, the lower the quality of the beverage and/or the fill level of the beverage, the shorter is the illuminated segment.

It is an advantage of the present invention that information may be displayed by beverage vessel in a manner that does not jeopardize the design of the beverage vessel.

It is an advantage of the present invention that quality of a beverage in a portable beverage vessel may be monitored. Further, a user can be provided with tailored beverages comprising the type of minerals and amount of minerals that are actually needed by the body of the user.

Further, the present invention avoids extensive use of plastic bottles, particularly one-way plastic bottles, harmful to the environment on land and sea. The comfort and contribution to the health according to the features of the present invention may convince a user to dispense with plastic bottles and use the inventive beverage vessel.

Although specific advantages have been enumerated above, various embodiments may include some, none, or all of the enumerated advantages. Other technical advantages may become readily apparent to one of ordinary skill in art after review of the following figures and description. It is understood that, although exemplary embodiments are illustrated in the figures and described below, the principles of the present disclosure may be implemented using any number of techniques, whether currently known or not. Modifications, additions, or omissions may be made to the systems, apparatuses, and methods described herein without departing from the scope of the invention. The components of the systems and apparatuses may be integrated or separated. The operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. It is intended that the claims and claim elements recited below do not invoke 35 U.S.C. 112(f) unless the words "means for" or "step for" are explicitly used in the particular claim. The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A method of controlling at least one of a beverage consumption and/or consumption of minerals in a beverage by a user of a portable beverage vessel for refilling a portable beverage vessel by a beverage dispenser, wherein the portable beverage vessel is positioned by a user for refilling at the beverage dispenser and wherein the beverage dispenser is adapted to cooperate with a plurality of beverage vessels, said method comprising the steps of transmitting at least one message to a beverage dispenser from a portable beverage vessel to be filled by the beverage dispenser;

identifying the portable beverage vessel by at least one message;

monitoring a temperature of air around the portable beverage vessel by using a vessel environment temperature sensor as part of the portable beverage vessel thereby determining the temperature of air surrounding the portable beverage vessel;

estimating the temperature of the beverage in the beverage vessel based on the temperature of air around the portable beverage vessel; and transmitting an estimation of the temperature of the beverage.

2. The method according to claim 1, further comprising the following steps:

exchanging messages between the beverage dispenser, the portable beverage vessel and a personal electronic device, wherein the personal electronic device and the beverage vessel are associated to the same user; and determining an amount and/or type of beverage to be recommended for drinking to the user based on the exchanged messages.

3. The method according to claim 1, comprising the steps of:

determining a physical activity of a user;

determining amount of beverage that has to be supplied to the user of the portable beverage vessel based on the physical activity of the user;

determining the type of minerals that have to be supplied to the user of the portable beverage vessel based on the physical activity of the user;

determining amount of minerals that have to be supplied to the user of the portable beverage vessel based on the physical activity of the user;

determining amount of beverage, the type of minerals and amount of minerals consumed by the user of the portable beverage vessel;

determining amount of beverage to be consumed by the user of the portable beverage vessel based on amount of beverage to be supplied to the user and amount of beverage consumed by the user;

determining the type of minerals to be consumed by the user of the portable beverage vessel based on the type of minerals to be supplied to the user and the type of minerals consumed by the user;

determining amount of minerals to be consumed by the user of the portable beverage vessel based on amount of minerals to be supplied to the user and the amount of minerals consumed by the user;

indicating to the user of the portable beverage vessel and/or the user of personal electronic device amount of beverage to be consumed.

4. The method according to claim 3, wherein the steps of determining the physical activity of a user;

determining amount of beverage to be supplied to the user of the portable beverage vessel;

determining the type of minerals to be supplied to the user of the portable beverage vessel; and determining amount of minerals to be supplied to the user of the portable beverage vessel;

are executed by the personal electronic device; and the step of determining amount of beverage, the type of minerals and amount of minerals consumed by the user of by the portable beverage vessel is executed by the portable beverage vessel.

5. The method according to claim 3, wherein the steps of indicating to the user of the portable beverage vessel and the user of the personal electronic device the type of minerals to be consumed; and indicating to the user of the portable beverage vessel and the user of the personal electronic device amount of minerals to be consumed;

are executed by a beverage dispenser adapted to fill the portable beverage vessel;

the personal electronic device; and/or the portable beverage vessel.

6. The method according to claim 3, further comprising at least one of the following steps proposing the user the type of minerals and amount of minerals by at least one of the following steps:

displaying on the beverage dispenser the proposed minerals and amount of minerals;

displaying on the personal electronic device the proposed minerals and amount of minerals;

displaying on the display of the portable beverage vessel the proposed minerals and amount of minerals.

7. The method according to claim 3, wherein the step of proposing the user the type of minerals and amount of minerals includes the step of displaying a symbol indicating the type of minerals and amount of minerals in the beverage.

8. The method of claim 1, comprising the following steps:

monitoring the temperature of air around the portable beverage vessel by the vessel environment temperature sensor;

generating a temperature profile of air around the portable beverage vessel during a predetermined time span; and determining a demand of a user for beverage and/or minerals based on a temperature profile.

9. A method of controlling at least one of a beverage consumption and/or consumption of minerals in a beverage by a user of a portable beverage vessel for refilling a portable beverage vessel by a beverage dispenser, wherein the beverage vessel is positioned by a user for refilling at the beverage dispenser and wherein the beverage dispenser is adapted to cooperate with a plurality of beverage vessels, said method comprising the steps of transmitting at least one message to a beverage dispenser from a portable beverage vessel to be filled by the beverage dispenser;

identifying the portable beverage vessel by at least one message;

monitoring the movement of the portable beverage vessel by a movement sensor comprised by the beverage vessel;

generating a movement profile of the portable beverage vessel during a predetermined time span; and determining a demand of a user for beverage and/or minerals based on the movement profile.

10. The method of claim 9, comprising the following steps:

monitoring the humidity of air around the portable beverage vessel by a vessel environment humidity sensor comprised by the beverage vessel;

generating a humidity profile of a temperature of air around the portable beverage vessel during a predetermined time span; and determining the demand of a user for beverage and/or minerals based on the humidity profile.

11. The method according to claim 9, further comprising the following steps:

exchanging messages between the beverage dispenser, the portable beverage vessel and a personal electronic device, wherein the personal electronic device and the beverage vessel are associated to the same user; and determining an amount and/or type of beverage to be recommended for drinking to the user based on the exchanged messages.

12. The method according to claim 9, comprising the steps of:
- determining a physical activity of a user;
- determining amount of beverage that has to be supplied to the user of the portable beverage vessel based on the physical activity of the user;
- determining the type of minerals that have to be supplied to the user of the portable beverage vessel based on the physical activity of the user;
- determining amount of minerals that have to be supplied to the user of the portable beverage vessel based on the physical activity of the user;
- determining amount of beverage, the type of minerals and amount of minerals consumed by the user of the portable beverage vessel;
- determining amount of beverage to be consumed by the user of the portable beverage vessel based on amount of beverage to be supplied to the user and amount of beverage consumed by the user;
- determining the type of minerals to be consumed by the user of the portable beverage vessel based on the type of minerals to be supplied to the user and the type of minerals consumed by the user;
- determining amount of minerals to be consumed by the user of the portable beverage vessel based on amount of minerals to be supplied to the user and the amount of minerals consumed by the user;
- indicating to the user of the portable beverage vessel and/or the user of personal electronic device amount of beverage to be consumed.

13. The method according to claim 12, wherein the steps of
- determining the physical activity of a user;
- determining amount of beverage to be supplied to the user of the portable beverage vessel;
- determining the type of minerals to be supplied to the user of the portable beverage vessel; and
- determining amount of minerals to be supplied to the user of the portable beverage vessel;
- are executed by the personal electronic device; and the step of
- determining amount of beverage, the type of minerals and amount of minerals consumed by the user of by the portable beverage vessel is executed by the portable beverage vessel.

14. The method according to claim 12, wherein the steps of
- indicating to the user of the portable beverage vessel and the user of the personal electronic device the type of minerals to be consumed; and
- indicating to the user of the portable beverage vessel and the user of the personal electronic device amount of minerals to be consumed;
are executed by
- a beverage dispenser adapted to fill the portable beverage vessel;
- the personal electronic device; and/or
- the portable beverage vessel.

15. The method according to claim 12, further comprising at least one of the following steps
- proposing the user the type of minerals and amount of minerals by at least one of the following steps:
- displaying on the beverage dispenser the proposed minerals and amount of minerals;
- displaying on the personal electronic device the proposed minerals and amount of minerals;
- displaying on the display of the portable beverage vessel the proposed minerals and amount of minerals.

16. The method according to claim 12, wherein the step of proposing the user the type of minerals and amount of minerals includes the step of
- displaying a symbol indicating the type of minerals and amount of minerals in the beverage.

17. The method of claim 9, comprising the following steps:
- monitoring the temperature of air around the portable beverage vessel;
- generating a temperature profile of air around the portable beverage vessel during a predetermined time span; and
- determining the demand of a user for beverage and/or minerals based on a temperature profile.

18. The method of claim 9, comprising the following steps:
- monitoring the humidity of air around the portable beverage vessel;
- generating a humidity profile of the temperature of air around the portable beverage vessel during a predetermined time span; and
- determining the demand of a user for beverage and/or minerals based on the humidity profile.

* * * * *